United States Patent [19]

Earl et al.

[11] 4,275,236

[45] Jun. 23, 1981

[54] TERTIARY DI-(β-HYDROXY ORGANO) AMINE OXIDES AND THEIR PREPARATION

[75] Inventors: Gary W. Earl, Bexley; Howard M. Hickman, Worthington, both of Ohio

[73] Assignee: Sherex Chemical Company, Inc., Dublin, Ohio

[21] Appl. No.: 106,746

[22] Filed: Dec. 26, 1979

[51] Int. Cl.$^3$ .............................................. C07C 135/02
[52] U.S. Cl. .................................. 564/298; 564/297; 564/299
[58] Field of Search ........... 260/583 D, 584 R, 584 B, 260/584 C; 564/297, 298, 299

[56] References Cited

U.S. PATENT DOCUMENTS

| | | | |
|---|---|---|---|
| 3,253,015 | 5/1966 | Hoffmann | 260/583 D X |
| 3,317,430 | 5/1967 | Priestley et al. | 260/583 D X |
| 3,366,632 | 1/1968 | Wakeman et al. | 260/583 D X |
| 3,449,432 | 6/1969 | Borstlap et al. | 260/584 R |
| 3,450,637 | 6/1969 | Drew | 260/584 R X |
| 3,501,335 | 3/1970 | Cahn et al. | 260/584 R X |
| 3,558,710 | 1/1971 | Stalioraitis et al. | 260/584 R |
| 3,872,116 | 3/1975 | Gipson | 260/583 D X |

FOREIGN PATENT DOCUMENTS

| | | | |
|---|---|---|---|
| 639398 | 4/1962 | Canada | 260/583 D |
| 2448641 | 4/1975 | Fed. Rep. of Germany | 260/583 D |

*Primary Examiner*—John Doll
*Attorney, Agent, or Firm*—Mueller and Smith

[57] ABSTRACT

Disclosed are tertiary amine oxides which comprise an amine oxide nucleus substituted with an organic group and with two hydroxy groups which have carbon atoms in at least the α, β and γ positions, a hydroxyl group on the β-carbon atom, and have an effective chain length of at least 4 carbon atoms, said amine oxide being capable of being provided in ostensibly anhydrous form and being capable of being made at a concentration by weight of at least about 80% by oxidizing the corresponding tertiary amine with an oxidizing agent without solvent and without gelling during said oxidation.

38 Claims, No Drawings

TERTIARY DI-(β-HYDROXY ORGANO) AMINE OXIDES AND THEIR PREPARATION

BACKGROUND OF THE INVENTION

The present invention relates to amine oxides and more particularly to new tertiary di-β-hydroxy amine oxides and their preparation.

Various aliphatic amine oxides presently are prepared commercially by oxidizing aliphatic tertiary amines with aqueous hydrogen peroxide. The tertiary amine is dissolved in solvent, preferably water, and reacted with a slight excess of aqueous hydrogen peroxide at temperatures of about 60° to 80° C. Conversions of the tertiary amine to the amine oxide routinely exceed 99%. Normally, these amine oxides are prepared as 30%–40% aqueous solutions. During the preparation of the amine oxides, the reaction mixture normally forms a gel which can last from one to several hours. Such gellation prevents efficient mixing of reagents and proper cooling of the reaction mixture. Moreover, the typically low amine oxide concentrations in the aqueous product means that a great deal of water is being handled and transported which clearly increases production and transportation costs. The water content of the aqueous amine oxides cannot be reduced readily as the product aliphatic amine oxides are hygroscopic.

BROAD STATEMENT OF THE INVENTION

One aspect of the present invention is a tertiary amine oxide which comprises an amine oxide nucleus substituted with an organic group and with two hydroxyl-bearing groups which have carbon atoms in at least the α, β, and γ positions, a hydroxyl group on the β-carbon atom, and have an effective chain length of at least four carbon atoms. Such tertiary amine oxides are capable of being provided in ostensibly anhydrous form and can be made at a concentration by weight of at least about 80% by oxidizing the corresponding tertiary amine with an oxidizing agent. No solvent is required during the oxidation reaction and no intermediate or final gellation is encountered during such oxidation reaction. The novel tertiary amine oxides can be represented by:

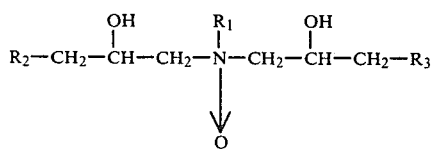

where each $R_1$, $R_2$, $R_3$, independently, is a monovalent group preferably containing at least one carbon atom.

Another aspect of the invention is a method for making the disclosed tertiary amine oxides which comprises forming a reaction mixture under oxidation conditions of an oxidizing agent and a tertiary amine represented by

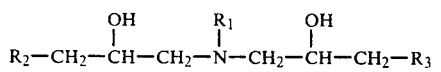

where each $R_1$, $R_2$, $R_3$, independently, is a monovalent group preferably containing at least one carbon atom. The reaction mixture does not gel during any stage of the oxidation reaction.

A further aspect of the present invention is an improved method for producing a tertiary amine oxide wherein a tertiary amine is oxidized with an oxidizing agent under oxidizing conditions. Such improvement comprises: forming a reaction mixture in a reaction zone held under oxidizing conditions in the substantial absence of added aqueous solvent of (a) a tertiary di-(β-hydroxy ethyl) amine, a tertiary di-(β-hydroxy propyl) amine or mixtures thereof;
(b) said oxidizing agent; and
(c) a stabilizing agent selected from

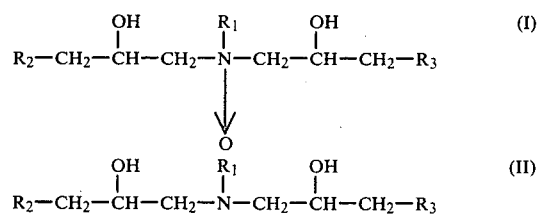

where each
$R_1$, $R_2$, $R_3$, independently, is a monovalent group preferably containing at least one carbon atom, said reaction mixture not gelling during said oxidizing of said tertiary amine; and withdrawing from said zone said tertiary amine oxide.

Advantages of the present invention include that the novel tertiary amine oxides can be prepared without added solvent and any water contained in such amine oxides from their production (i.e. by-product water and any water from an aqueous oxidizing agent) can be removed readily as such amine oxides appear to be non-hygroscopic. Also, during the preparation of such novel tertiary amine oxides, no intermediate gel stage of the reaction mixture is encountered which improves mixing efficiency and heat removal from the reaction mixture during the oxidation reaction. Further, such novel tertiary amine oxides can be used as stabilizers for oxidizing tertiary amines which without the presence of such stabilizing agent can be prepared only in dilute aqueous concentrations and even then still pass through an intermediate gellation stage during their preparation. The incorporation of the novel amine oxide stabilizing agent dispenses with the need for added aqueous solvent and substantially suppresses any intermediate gel formation. These and other advantages will become readily apparent from the disclosure of the invention contained herein.

DETAILED DESCRIPTION OF THE INVENTION

As noted above, tertiary di-(β-hydroxy propyl or ethyl) amines when oxidized proceed through an intermediate gel stage which causes mixing problems, localized overheating with possible attendant decomposition, and like problems. Thus, such amines must be diluted in water in order to make at most about a 40% solids amine oxide aqueous product. Moreover, once the aqueous amine oxide product is made, water cannot be readily stripped therefrom, if at all, as such amine oxides apparently are rather hygroscopic. The attempted removal of water, instead, usually results in the formation of a viscous gel that eventually solidifies.

The foregoing should be contrasted with the novel amine oxides of the present invention which can be prepared by oxidizing the corresponding tertiary amines without added solvent, and any water remaining in the resulting amine oxide product usually can be removed readily as such amine oxides appear to be non-hygroscopic. Additionally, during the oxidation reaction, the reaction mixture does not pass through an intermediate gel stage which means that efficient mixing and heat removal can be practiced. The simplest novel amine oxide of the present invention is a tertiary di-(β-hydroxy butyl) amine oxide. As will be demonstrated in the Examples which follow, such β-hydroxy butyl amine oxide can be formed from a reaction mixture of the corresponding tertiary amine and an oxidizing agent without added solvent and the reaction mixture not proceed through an intermediate gel stage. Moreover, it has been shown that any water in the product amine oxide can be stripped readily and that the amine oxide product is non-hygroscopic. Thus, the apparent mere increase of chain length, even only of one carbon atom, has caused a quantum change in the chemical and physical properties of the resulting amine oxide. Such quantum change in properties is totally unexpected by such mere increase of chain length. The reasons for the stability of the novel amine oxides are not fully understood presently, though the following hypothesis particularly illustrated by the hydroxy butyl amine oxide of the present invention is offered. It is understood that the following hypothesis is not a limitation of the present invention and the use of the hydroxy butyl amine oxide is for purposes of illustration only. Thus, it is theorized that the stability of the hydroxy butyl amine oxide derivatives may be based on the bicyclic hydrogen-bonded structure postulated below.

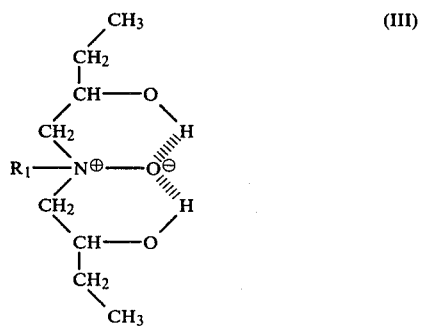

(III)

Whether the side chain ethyl groups act as steric interference for water approach to the alcohol groups or the hydroxy butyl groups simply change the hydrophilic nature of the polar end of the molecule (or the HLB) has not been established definitively. Nevertheless, the 11%–12% water present at the end of the oxidation step (assuming the use of a 50% aqueous peroxide oxidizing agent in addition to the one equivalent of water derived from the hydrogen peroxide oxidation itself) can be stripped easily merely using a water aspirator at the reaction temperature.

From examination of molecular models, it can be seen that the terminal methyl group of the hydroxy butyl group is directed towards the hydroxyl group and, therefor, must discourage the approach of water molecules. From the following diagrams

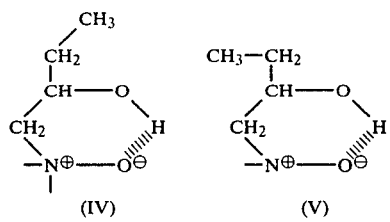

it appears that free rotation about the CH—CH₂ bond should permit the terminal methyl group to move away from the alcohol group. In fact, however, the molecular model of such compound shows the terminal methyl group experiences tremendous steric strain when in position (V) above and must remain in the area of the hydroxyl group as shown in position (IV) above. The fact that the novel amine oxides are non-hygroscopic seems credible based on the foregoing structural arrangement and hypothesis. Regardless of the underlying theory explaining the stability of the novel amine oxides, the novel tertiary amine oxides of the present invention and their properties have been defined and will be fully disclosed herein.

The tertiary amine oxides of the present invention comprise an amine oxide nucleus substituted with an organic group and with two hydroxyl-bearing groups which have carbon atoms in at least the α, β, and γ positions, a hydroxyl group on the β-carbon atom, and an effective chain length of at least four carbon atoms. By "amine oxide nucleus" is meant the nitrogen-oxygen moiety wherein the nitrogen atom contains three additional substituents. While the two hydroxyl-bearing groups in theory may be dissimilar, practical problems of synthesizing substantially pure amine oxides with different hydroxyl-bearing groups, especially on a commercial scale, dictate that such hydroxy-bearing groups be the same.

The novel tertiary amine oxides of the present invention can be represented generally by the following structure:

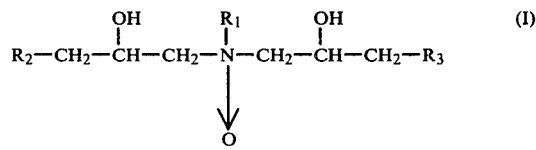

(I)

where each $R_1$, $R_2$, $R_3$, independently, is a monovalent group preferably containing at least one carbon atom. Broadly, $R_1$ is a linear or branched, substituted or unsubstituted, saturated or unsaturated monovalent aliphatic, alicyclic, alicyclicaliphatic, or aliphatic-aromatic group which may contain linkages of ether, amine, amide, or sulfide. Advantageously, $R_1$ is a $C_1$–$C_{30}$ alkyl or ether alkyl group. Presently preferred $R_1$ groups include $C_4$–$C_{22}$ alkyl ether trimethylene groups and $C_4$–$C_{22}$ alkyl groups.

Preferably, $R_2$ and $R_3$ are the same. $R_2$ and $R_3$ should not be readily displaced or reactive during the oxidation reaction (e.g. not a halide) in order to suppress degradation by-products and increase the yield of the desired tertiary amine oxide. Appropriate non-reactive groups, then, could be a nitrile group, a thioether group, an amide group, or the like; however, hydrocarbyl groups are preferred. Thus, $R_2$ and $R_3$ preferably are a $C_1$–$C_{22}$ alkyl or alkyl ether groups.

In connection with possible degradation by-products produced during the oxidation reaction, it should be understood that some of the tertiary amines used for producing the novel amine oxides of the present invention or the resulting amine oxides themselves may tend to yield small proportions, e.g. up to 15%, of degradation by-products, though the resulting amine oxides still are ostensibly anhydrous and are produced without any intermediate gellation occurring during the oxidation reaction. Occasionally, the product amine oxides may be sensitive to further processing conditions, for example, wherein water is stripped from the amine oxide product, and minor proportions of degradation by-products additionally occur. Even under such circumstances, the amine oxides produced are within the scope of the present invention as they can be provided in an ostensibly anhydrous form and are produced by the oxidation reaction without intermediate gellation occurring.

In making the novel tertiary amine oxides of the present invention, it should be understood that the reaction can be conducted with added solvent, usually water though possibly an alcohol or aqueous alcohol may be used. However, the need for added solvent is abrogated which contributes to the efficiency and economy of producing the amine oxides. By "added solvent" is meant that a volume of solvent is not added to the reaction mixture for producing the amine oxides. Added solvent does not include any adventitious sources of water entering the reaction mixture nor the water produced during the oxidation reaction nor any water originally found in the oxidizing agent as aqueous oxidizing agents are common and preferred for use in the present invention as will be described further below. Accordingly, the total water content of the reaction mixture should be less than about 20% and preferably less than about 10% by weight. By ostensibly or essentially anhydrous is meant that the water content of the amine oxides will be at most about 10%, advantageously not substantially more than about 5% and preferably not substantially more than about 1%. It should be recognized, however, that to provide such anhydrous amine oxide product, some particular amine oxides may be sensitive to processing for water removal (as noted above). Such amine oxides could be provided in essentially anhydrous form if extra by-product formation were tolerable, though removal of all water with possible attendant by-product formation usually is not necessary as the low (about 11%–12% at most) water content of the product can be tolerated for most uses of the product.

The tertiary amine oxides are made by forming a reaction mixture under oxidizing conditions of an oxidizing agent and the corresponding tertiary amine. The preferred oxidizing agent is a peroxidizing agent, such as hydrogen peroxide, typically provided in aqueous form. Oxidation conditions comprehend typically temperatures of about 60°–80° C. or thereabouts under subatmospheric, atmospheric or superatmospheric pressure as is necessary, desirable, or convenient. Normally, the molar or equivalent (abbreviated eq. often herein) ratio of oxidizing agent to tertiary amine is slightly in excess of 1. It should be noted, that peracids additionally may be used as the oxidizing agent (see March, *Advanced Organic Chemistry*, Second Edition, page 1111, McGraw-Hill Publishing Company, New York, 1977). Reaction times can range from as short as a few hours on up to 10–15 hours or more depending upon the oxidation conditions and particular reactants used. At the termination of the oxidation reaction, the water formed from the peroxidizing agent and any additional water in the reaction mixture from advantitious sources or from the peroxidizing agent itself can be removed simply by reducing pressure of the reaction mixture at reaction temperature or by similar conventional techniques.

The resulting novel amine oxide product typically has an amine oxide solids content of at least about 80%, advantageously at least about 90%, and preferably at least about 95% by weight. The product amine oxide can be stored and used in such concentrated form or can be diluted in a volume of water. It should be noted that when the amine oxide is diluted in water that in order to stabilize the aqueous amine oxide and suppress phase separation, that a protic acid must be added thereto as is disclosed in applicants' commonly assigned application U.S. Ser. No. 106,747 filed on Dec. 26, 1979 entitled "Stabilization of Aqueous Tertiary Di-$\beta$-Hydroxy Amine Oxides." Note also that for long term color stability of the concentrated amine oxide product that it appears presently that an excess of free hydrogen peroxide (and/or minor proportion of protic acid) should be incorporated therein, though this is presently not fully confirmed.

The novel amine oxide product finds wide use as a wetting agent, surfactant, or dispersant. Accordingly, the novel amine oxides may be used as foaming agents or foam stabilizers in shampoos or liquid dishwashing detergents, as froth stabilizers in the froth flotation of mineral ores (e.g. the froth flotation of sylvite from sylvinite), and similar uses. Additionally, an alkyl ether di($\beta$-hydroxy butyl) amine oxide derivative has been determined to be effective as a foam stabilizer for stabilizing a foam of alkyl benzene sulfonate foaming agent as shown in Examples II-V, inclusive, of the commonly assigned patent application of Egan and Watts, U.S. Ser. No. 6/052,665, filed June 27, 1979, and entitled "Amine Oxide Foam Stabilizers for Alkyl Benzene Sulfonate Foaming Agents," the disclosure of which is expressly incorporated herein by reference.

Another use developed for the novel amine oxides is as a stabilizing agent in the oxidation of tertiary di-($\beta$-hydroxy ethyl) amines and tertiary di-($\beta$-hydroxy propyl) amines. As noted above, the hydroxy ethyl and hydroxy propyl amine oxide derivatives cannot be produced at high solids concentration, are hygroscopic, and even in dilute aqueous dispersion proceed through an intermediate gel phase during their production. However, use of the amine oxides of the present invention, or the corresponding tertiary amines from which they are derived, permits production of such hydroxy ethyl and hydroxy propyl amine oxides without the need for added solvent and without the reaction mixture passing through an intermediate gel stage. The Examples will further amplify this aspect of the present invention.

The following Examples show how the present invention can be practiced, but should not be construed as limiting. In this application, all percentages and proportions are by weight and all units are in the metric system, unless otherwise expressly indicated.

EXAMPLE I

A di-(β-hydroxy butyl) amine was prepared by reacting ADOGEN 185 fatty amine [$(C_{12-15})$-O-$(CH_2)_3$-$NH_2$, MW of about 275–289, supplied by Sherex Chemical Company, Inc., Dublin, Ohio, ADOGEN being their registered trademark] with 2.1 equivalents of butylene oxide in a Parr bomb at 175° C. under a pressure of 50 psig. The butylene oxide addition required 1.5 hours and was followed by an additional 1 hour cook. The resulting tertiary amine analyzed at 99.7% (Gardner color 4+) and its structure was confirmed by infrared spectroscopy (IR) and nuclear magnetic resonance (NMR) techniques.

A lot of the resulting tertiary amine was oxidized with 1.1 equivalents of $H_2O_2$ at 70° C. for 1 hour and stripped for 1 hour at the same temperature. The resulting amine oxide analyzed 99.4% amine oxide and 0.5% free amine by titration. The reaction mixture never passed through a gel stage during the oxidation reaction. The amine oxide product (pH of about 8–8.5) was adjusted to pH 6.5 with HCl and has remained a clear one phase system for over 8 months. Note, that use of water or other compatible solvent for the oxidation does not alter these results.

Aliquots of the unneutralized amine oxide were titrated in both isopropyl alcohol (IPA) and water/IPA (equal weight proportions). Titration curves revealed that at the equivalence point, 1.0 equivalent of HCl is consumed by 1.0 equivalent of the amine oxide. The equivalence point of the amine oxide in IPA was pH 2.3 and in water/IPA it was pH 3.0. Since a pH range of 5.5 to 6.5 is preferred for stabilizing the amine oxide in water the following titration data is important.

| pH | % Protonated Amine Oxide | |
| --- | --- | --- |
|  | IPA | $H_2O$/IPA |
| 5.5 | 45 | 36 |
| 6.5 | 14 | 21 |

Thus, it requires about 10% protonated tertiary di(β-hydroxy organo) amine oxide to stabilize the tertiary di-(β-hydroxy organo) amine oxides of the present invention.

As shown above, the preferred amine oxides of the present invention can be prepared in ostensibly anhydrous form. In order to evaluate the hygroscopic character of the amine oxides, a thin-film sample (about 2 grams coated uniformly on a 7.62 cm diameter dish) of the stabilized and dried (99.4%) amine oxide was subjected to the atmosphere for 6.5 hours. The sample gained only 1.2 mg (0.05%). Another thin-film sample of the un-neutralized, unstripped amine oxide lost 7.6 mg (0.38%). Thus, the amine oxide appears not to be hygroscopic in nature.

In order to accentuate the unique properties of the present amine oxides, viz the importance of the two β-hydroxy groups of at least 4 carbon atoms, a sample of the ADOGEN 185E amine was reacted with ethylene oxide in order to add two β-hydroxy ethyl groups to the nitrogen atom. This 99.4% tertiary amine was oxidized with $H_2O_2$ at 70° C. under a nitrogen blanket without added solvent. However, the reaction mixture began to gel within 15 minutes reaction time, could not be agitated effectively, and exhibited localized and overall overheating problems. After 2 hours reaction time, the reaction mixture began to darken and eventually became a dark (Gardner color of 16) gel which titrated for 72.0% amine oxide and 5.8% free amine. The product theoretically should have titrated for in excess of 85% amine oxide plus free amine. Thus, 10%–15% of the product had decomposed to non-titratables. Similar results have been obtained also when oxidizing dimethyl and di-β-hydroxy propyl amine oxides containing a lauryl group or a $C_{12}$–$C_{15}$ ether trimethylene group. Only when the chain length of the β-hydroxy alkyl group exceeds 4 carbon atoms in effective chain length can a stable, non-gelled amine oxide be prepared at high solids concentration without solvent. The above-comparative amine oxides require dilution with water to about 40% solids maximum of oxides to obtain a clear product and even then intermediate gel stages occur during the oxidation reaction.

EXAMPLE II

One mole of tridecyl ether trimethylene amine was alkoxylated with 2.2 equivalents of butylene oxide at 175° C. and 50 psig. Oxidation of the resulting tertiary amine with $H_2O_2$ (1.1 eq.) at 70° C. yielded upon evaporation of water an amine oxide (Gardner color 1) analyzing for 99.6% amine oxide and 0.2% free amine. No intermediate gel stage was encountered during the peroxidation reaction. The clear, pale-yellow product was stable for 3 months.

EXAMPLE III

Two moles of hydrogenated tallow amine was butoxylated at 175° C. and 50 psig with 2.2 equivalents of butylene oxide. The 99.2% tertiary amine product was oxidized with 1.2 equivalents of $H_2O_2$ at 70° C. to yield a 96.6% amine oxide, 1.60% free amine product. Again, no intermediate gel stage was experienced. The amine oxide product was neutralized to pH 6.0, stripped for 1.5 hours at 70° C. to remove water, and flaked.

EXAMPLE IV

One mole of lauryl amine (99.2% primary $C_{12}$ amine, secondary and tertiary amine value=0) was butoxylated with 2.1 equivalents of butylene oxide at 175°–185° C. and 50 psig for 4 hours to yield a 98.4% tertiary product. Oxidation of the tertiary amine with 1.1 eq. of 50% $H_2O_2$ at 65° C. yielded a product analyzing 82.1% amine oxide and 1.43% free amine upon 3 peroxide adjustments and stripping of water. No intermediate gel stage was experienced. Water analysis showed the solidified amine oxide product to contain only 2.51% water. Thus, about 14% of the product apparently was untitratable nitrogen.

A slight blue-green cast in the product was identified by Atomic Absorption as 3.2 ppm Ni, 0.12 ppm Cr, and 1.6 ppm Cu, apparently originating from the original lauryl amine. After removal of these contaminants (Fitrol 13 filter agent and charcoal), oxidation of the clean tertiary amine yielded a product analyzing 90.5% amine oxide and 5.8% free amine. Upon peroxide adjustment and stripping, the product analyzed 84.4% amine oxide and 5.2% free amine. Apparently some variation of a Cope elimination must have occured during the processing of the product.

EXAMPLE V

A sample (0.7 moles) of octyl ether trimethylene amine was butoxylated with 2.34 equivalents of butylene oxide at 195° C. and 50 psig to yield a 99.2% tertiary amine (Gardner color of 2). This tertiary amine was oxidized with 1.15 eq. of 50% $H_2O_2$ in the absence of solvent without any intermediate gel stage occurring. The resulting stripped amine oxide (Gardner color of 1) titrated for 96.3% amine oxide and 1.2% free amine.

EXAMPLE VI

Hexyl amine (1.5 moles) was reacted with α-hexadecene oxide (3.125 moles or 2.2 eq.) in a Parr bomb at 175° C. and 50 psig. After 15 hours reaction time, the product analyzed at 98.8% tertiary amine. The tertiary amine was oxidized without solvent using 1.1 eq. of 50% $H_2O_2$. No intermediate gel stage was experienced. After 3 hours reaction time, the product analyzed by titration to contain 92.2% amine oxide and 0.3% free amine. The product was stripped of water and solidified upon cooling as expected (m.p. 69°–72° C.). The product analyzed to contain only 0.64% residual water.

EXAMPLE VII

Since the tertiary di-($\beta$-hydroxy butyl) amine derivatives oxidize without passing through an intermediate gel stage and the resulting amine oxides concentrate to extremely high solids content, it was desired to determine whether such butoxylated amines could be used to produce propoxylated or ethoxylated amine oxides at high solids content without gel formation by some chemical or physical action (e.g. entrainment). Thus, a mixture (50 g. each) of the butoxylated and ethoxylated tertiary amines of Example I was oxidized with 1.1 eq. of $H_2O_2$ without the use of any solvent. The oxidation was conducted at 70° C. for 2 hours during which time no gel formed. The stripped product analyzed to contain 98.3% total amine oxide and only 0.3% free amine. Thus, the amine oxides of the present invention can be used to produce high solids amine oxides without gel formation from tertiary amines which otherwise could not be so produced.

As a further evaluation, half of the resulting mixed amine oxide product was added to an additional 100 grams of the ethoxylated tertiary amine and this mixture reacted with 1.1 eq. of 50% $H_2O_2$. Again, no gel formed during 2 hours reaction time at 70° C. Upon stripping the product for 1 hour, it titrated to contain 91.3% total amine oxide and only 2.7% free amine. Thus, the amine oxide mixture was highly effective in assisting in the production of a relatively high solids ethoxylated amine oxide and totally effective in suppressing any gel formation during the oxidation step in producing the ethoxylated amine oxide product.

EXAMPLE VIII

Dramatic physical and chemical property differences have been demonstrated for equivalent di-($\beta$-hydroxy butyl) and di-($\beta$-hydroxy propyl or ethyl) amine oxides. It would be interesting, then, to determine the properties of a di-($\beta$-hydroxy isobutyl) amine oxide which in structure is intermediate between the hydroxy propyl and hydroxy butyl amine oxides.

The fatty amine of Example I (0.69 moles) was reacted with isobutylene oxide (2.25 eq.) at 205° C. and 50 psig. Oxide addition required 5 hours and the reaction temperature was higher than that required for the straight chain isomer. The product (Gardner color of 6 and 99.1% tertiary amine) was oxidized with 1.23 eq. of $H_2O_2$ in the presence of Versene 100 sequestering agent (a sodium salt of ethylene diamine tetraacetic acid supplied by Dow Chemical Company, Midland, Mich., Versene being their registered trademark). The stripped amine oxide product analyzed 85.9% amine oxide and 1.9% free amine. Though no gel stage was experienced during the oxidation of the tertiary amine (like the $\beta$-hydroxy butyl amine oxide analog), the product amine oxide could not be converted to an essentially anhydrous form (like the $\beta$-hydroxy propyl and ethyl amine oxides).

Thus, the physical and chemical properties of the $\beta$-hydroxy isobutyl derivative lie intermediate the $\beta$-hydroxy butyl and propyl derivatives as does its structure.

EXAMPLE IX

It would be interesting to determine the effect which the $\beta$-hydroxy group on the butyl substitutents of the tertiary amine displays in the oxidation reaction. Thus, 0.26 moles of tallow dibutyl amine (analyzing 93.5% tertiary amine, 2% secondary amine, and 4% primary amine) was reacted with 1.38 eq. of $H_2O_2$ at 50° C. for 5 hours without use of solvent. The product amine oxide analyzed at 55.4% amine oxide and 14.4% free amine. Still, no gel formed during the reaction.

A second oxidation was conducted in the presence of 1.5% Versene 100 sequestering agent and a total of 1.81 eq. of $H_2O_2$. No gel stage was encountered during the oxidation. The amine oxide product analyzed at 58.5% amine oxide and 17.1% free amine. This product had the distinct odor of butene. Thus, a Cope elimination reaction apparently is occurring at the chosen reaction temperatures and likely the free amine being titrated is the Cope product, N-hydroxy tallow butyl amine.

Clearly, then, these results demonstrate that the $\beta$-hydroxy groups not only assist in stabilizing the amine oxide products, but also are instrumental in the formation of such products.

EXAMPLE X

Further evaluation of different types of the $\beta$-hydroxy groups was undertaken. The primary ether amine in Example I (0.5 mole) was reacted with 2.1 eq. of t-butyl glycidyl ether in glass at 100° C. by the dropwise addition of the glycidyl ether over a 1.5 hour period. The reaction was essentially complete in 7 hours reaction time. The tertiary amine product (Gardner color of 3) was oxidized with 1.1 eq. of 50% $H_2O_2$ without solvent at a temperature not exceeding 70° C. No gel stage was encountered. After 3 hours reaction time, the product titrated for 91% amine oxide and 0% free amine.

Upon stripping the product at 60° C. for 1 hour using a water aspirator, the product titrated for 89.1% amine oxide and 3.54% free amine. A peroxide adjustment converted the product to 89.1% amine oxide and 1.0% free amine. However, upon stripping, the free amine content rose to 2.4% (86.6% amine oxide). Water analysis showed the product to contain only 0.77% water. Clearly, the tertiary amine oxidized well, but the resulting amine was unstable under the stripping conditions employed.

Consequently, the oxidation was repeated using 1.1 eq. of 50% $H_2O_2$ and 0.5 g. (0.5%) Versene 100 agent. Again, no gel stage occurred. Titration showed the product for 89.1% amine oxide and 0.85% free amine. This time, however, the product was stripped on a Buchler evaporator at 40° C. maximum temperature for 1 hour and filtered to yield a product (Gardner color of 1+) titrating for 85.1% amine oxide and 8.0% free amine.

Thus, the tertiary amine was oxidized easily with no gel stage to a rather high solids content (about 90%), but the amine oxide product was unstable under the stripping conditions employed. It is theorized that the titratable material in the stripped product may not be free amine, but rather a t-butoxide anion formed by a "Cope-type" elimination reaction, i.e.

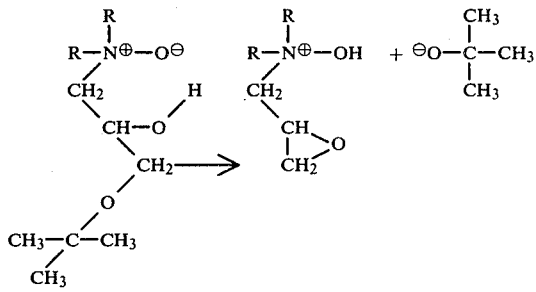

Although, the t-butoxide radical is not nucleophilic, it certainly could be titrated with HCl.

EXAMPLE XI

ADOGEN 185 amine of Example I was reacted with 2.1 eqs. of styrene oxide at 120° C. in glass for 20 hours under atmospheric pressure to produce a 99.4% tertiary amine having the following structure:

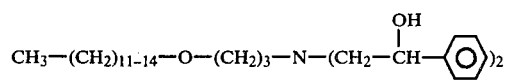

The amine had a Gardner color of 1⁻ and its structure was confirmed by IR and NMR.

Oxidation of this tertiary amine (MW range of 515–529) proceeded with 1.1 eq. of 50% aqueous $H_2O_2$ at 60° C. without added solvent followed by stripping of the product under vacuum for 1 hour at the reaction temperature. The reaction mixture never passed through any intermediate gel stage during the oxidation reaction. The final product analyzed for 98.1% amine oxide, 1.4% free amine, and 0.4% water.

Again, the present invention is demonstrated. Note that for long term stability of the resulting amine oxide in water, the pH thereof preferably is adjusted from an initial 7.8 to a pH of 5.7 with concentrated HCl as taught in application Ser. No. 106,747, filed Dec. 26, 1979, cited above.

We claim:

1. A tertiary amine oxide comprising an amine oxide nucleus substituted with an organic group and with two hydroxy substituted organic groups which have carbon atoms in at least the α, β and γ positions, a hydroxyl group on the β-carbon atom, and have an effective chain length of at least 4 carbon atoms, said amine oxide being capable of being provided in ostensibly anhydrous form and being capable of being made at a concentration by weight of at least about 80% by oxidizing the corresponding tertiary amine with an oxidizing agent without solvent and without gelling during said oxidization.

2. The tertiary amine oxide of claim 1 wherein said organic group is a linear or branched, substituted or unsubstituted, saturated or unsaturated monovalent aliphatic, alicyclic, or aliphatic-aromatic group which may contain linkages of ether, amine, amide, or sulfide.

3. The tertiary amine oxide of claim 2 wherein said organic group is a $C_1$–$C_{30}$ alkyl or alkyl ether group.

4. The tertiary amine oxide of claim 3 wherein said organic group is a $C_4$–$C_{22}$ alkyl ether or alkyl group.

5. The tertiary amine oxide of claim 1 wherein said two hydroxy substituted organic groups are the same.

6. The tertiary amine oxide of claims 1, 4, or 5 wherein said hydroxy substituted organic groups are $C_4$–$C_{22}$ alkyl or alkyl ether groups with a hydroxyl group on the β-carbon atom.

7. A tertiary amine oxide represented by:

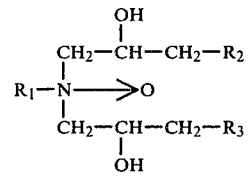

wherein each $R_1$, $R_2$, $R_3$, independently, is a monovalent group containing at least one carbon atom.

8. The tertiary amine oxide of claim 7 wherein $R_1$ is a linear or branched, substituted or unsubstituted, saturated or unsaturated monovalent aliphatic, alicyclic, or aliphatic-aromatic group which may contain linkages of ether, amine, amide, or sulfide.

9. The tertiary amine oxide of claim 8 wherein $R_1$ is a $C_1$–$C_{30}$ alkyl or alkyl ether group.

10. The tertiary amine oxide of claim 9 wherein $R_1$ is a $C_4$–$C_{22}$ alkyl ether or alkyl group.

11. The tertiary amine oxide of claims 1 or 10 wherein $R_2$ and $R_3$ are $C_1$–$C_{22}$ alkyl or alkyl ether groups.

12. The tertiary amine oxide of claim 11 wherein $R_2$ and $R_3$ are the same.

13. A method for making a tertiary amine oxide product which comprises forming a reaction mixture under oxidation conditions of an oxidizing agent and a tertiary amine represented by:

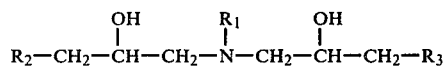

where each $R_1$, $R_2$, $R_3$, independently, is a monovalent group containing at least one carbon atom, said reaction mixture not gelling during said reaction.

14. The method of claim 13 wherein no solvent is used in forming said reaction mixture.

15. The method of claim 13 wherein said oxidizing agent is a peroxide.

16. The method of claim 15 wherein said peroxide is hydrogen peroxide.

17. The method of claim 15 wherein said peroxide is provided in aqueous form.

18. The method of claim 13 wherein said product contains not substantially in excess of 15% by weight of water.

19. The method of claim 13 wherein said product is stripped of substantially all of its water content.

20. The method of claim 13 wherein said product contains at least about 80% of said tertiary amine oxide by weight.

21. The method of claim 13 wherein $R_1$ is a linear or branched, substituted or unsubstituted, saturated or unsaturated monovalent aliphatic, alicyclic, or aliphatic-aromatic group which may contain linkages of ether, amine, amide, or sulfide.

22. The method of claim 21 wherein $R_1$ is a $C_1$-$C_{30}$ alkyl or alkyl ether group.

23. The method of claim 22 wherein $R_1$ is a $C_4$-$C_{22}$ alkyl ether or alkyl group.

24. The method of claims 13 or 23 wherein $R_2$ and $R_3$ are $C_1$-$C_{22}$ alkyl or alkyl ether groups.

25. The method of claim 24 wherein $R_2$ and $R_3$ are the same.

26. In a method for producing a tertiary amine oxide product wherein a tertiary amine is oxidized with an oxidizing agent under oxidizing conditions, the improvement comprising:

forming a reaction mixture in a reaction zone held under said oxidizing conditions in the substantial absence of added aqueous solvent of
(a) a tertiary di-($\beta$-hydroxy ethyl) amine, a tertiary di-($\beta$-hydroxy propyl) amine, or mixtures thereof;
(b) said oxidizing agent; and
(c) a stabilizing agent selected from

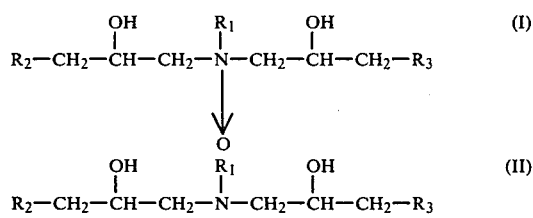

where each
$R_1$, $R_2$, $R_3$, independently, is a monovalent group containing at least one carbon atom, said reaction mixture not gelling during said oxidizing of said tertiary amine; and withdrawing from said zone said tertiary amine oxide product.

27. The method of claim 26 wherein said reaction mixture contains not substantially in excess of 15% of weight of water.

28. The method of claim 26 wherein said oxidizing agent is a peroxide.

29. The method of claim 28 wherein said peroxide is hydrogen peroxide.

30. The method of claim 29 wherein said peroxide is provided in aqueous form.

31. The method of claim 26 wherein the third substituent of said tertiary di-($\beta$-hydroxy ethyl) amine and said tertiary di-($\beta$-hydroxy propyl) amine is $R_1$.

32. The method of claims 26 or 31 wherein $R_1$ is a linear or branched, substituted or unsubstituted, saturated or unsaturated monovalent aliphatic, alicyclic, or aliphatic-aromatic group which may contain linkages of ether, amine, amide, or sulfide.

33. The method of claim 32 wherein $R_1$ is a $C_1$-$C_{30}$ alkyl or alkyl ether group.

34. The method of claim 33 wherein $R_1$ is a $C_4$-$C_{22}$ alkyl ether or alkyl group.

35. The method of claim 34 wherein $R_2$ and $R_3$ are $C_1$-$C_{22}$ alkyl or alkyl ether groups.

36. The method of claim 34 wherein $R_2$ and $R_3$ are the same.

37. The method of claim 26 wherein $R_2$ and $R_3$ are $C_1$-$C_{22}$ alkyl or alkyl ether groups.

38. The method of claim 37 wherein $R_2$ and $R_3$ are the same.

* * * * *